US00PP19970P3

(12) United States Plant Patent
Meilland

(10) Patent No.: US PP19,970 P3
(45) Date of Patent: Apr. 28, 2009

(54) HYBRID TEA ROSE PLANT NAMED 'MEITRONI'

(50) Latin Name: *Rosa hybrida*
Varietal Denomination: Meitroni

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 66 days.

(21) Appl. No.: 11/822,398

(22) Filed: Jul. 5, 2007

(65) Prior Publication Data

US 2008/0307550 P1 Dec. 11, 2008

(51) Int. Cl.
*A01H 5/00* (2006.01)

(52) U.S. Cl. ..... Plt./137

(58) Field of Classification Search ..... Plt./137
See application file for complete search history.

*Primary Examiner*—Kent L Bell
(74) *Attorney, Agent, or Firm*—Buchanan Ingersoll & Rooney PC

(57) ABSTRACT

A new and distinct variety of Hybrid Tea rose plant is provided that forms at mid-season abundantly and substantially continuously attractive highly fragrant Orient Pink blossoms. The buds are substantially conical-shaped. The vegetation is very strong and attractive glossy dark green foliage is formed. Excellent resistance to Marsonia is displayed. The plant is particularly well suited for providing attractive ornamentation in the landscape.

1 Drawing Sheet

Botanical/commercial classification: *Rosa hybrida*/Hybrid Tea Rose Plant.
Varietal denomination: cv. Meitroni.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Tanrowisa' variety (non-patented in the United States) and the 'Meimalyna' variety (non-patented in the United States). The male parent (i.e., the pollen parent) was the 'Harkuly' variety (non-patented in the United States). The 'Harkuly' variety sometimes is known as the 'Margaret Merril' variety.

('*Tanrowisa*'×'*Meimalyna*')×'Harkuly'.

The seeds resulting from the above pollination were sown and small plants were obtained which were physically and biologically different from each other. Selective study resulted in the identification of a single plant of the new variety.

It was found that the new Hybrid Tea rose plant of the present invention:

(a) forms very strong vegetation, (b) forms large substantially conical-shaped buds, (c) forms at mid-season abundantly and substantially continuously attractive highly fragrant Orient Pink blossoms, (d) displays attractive glossy dark green foliage, (e) displays excellent resistance to Marsonia, (f) is particularly well suited for providing attractive ornamentation in the landscape.

The new variety well meets the needs of the horticultural industry and can be grown to advantage in parks and gardens. The disease tolerance is good particularly with respect to Marsonia.

The new variety can be readily distinguished from its ancestors. For instance, the blossom coloration is considerably different from that of the 'Tanrowisa', 'Meimalyna', and 'Harkuly' varieties. More specifically, the 'Tanrowisa' variety forms blossoms that are pink on the upper surface and silver on the under surface, the 'Meimalyna' variety forms medium red blossoms, and the 'Harkuly' variety forms white blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meitroni'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during May while budded on *Rosa laxa* understock and growing outdoors at Le Cannet des Maures, Var, France. Dimensions in centimeters are indicated at the bottom of the photograph, as is a standard color comparison.

FIG. 1 — illustrates a specimen of a bud before the opening of the sepals;

FIG. 2 — illustrates a specimen of a floral bud at the opening of the sepals;

FIG. 3 — illustrates a specimen of a floral bud at the opening of the petals;

FIG. 4 — illustrates a specimen of a flower in the course of opening;

FIG. 5 — illustrates a specimen of an open flower — plan view — obverse;

FIG. 6 — illustrates a specimen of an open flower — plan view — reverse;

FIG. 7 — illustrates a specimen of a fully open flower — plan view — obverse;

FIG. 8 — illustrates a specimen of a fully open flower — plan view — reverse;

FIG. 9 — illustrates a specimen of a floral receptacle showing the arrangement of the stamens and pistils;

FIG. 10 — illustrates a specimen of a floral receptacle showing the pistils (stamens removed);

FIG. 11 — illustrates a specimen of a flowering stem;

FIG. 12 — illustrates a specimen of a main branch;

FIG. 13 — illustrates a specimen of a leaf with three leaflets — plan view — upper surface;

FIG. 14 — illustrates a specimen of a leaf with five leaflets — plan view — under surface; and FIG. 15 — illustrates a specimen of a leaf with seven leaflets — plan view — upper surface.

DETAILED DESCRIPTION

The chart used in the identification of the colors is that of the Royal Horticultural Society (R.H.S. Colour Chart). The description is based on the observation of one-year-old plants during May which were budded on *Rosa laxa* understock and growing outdoors at Le Cannet des Maures, Var, France.

Class: Hybrid Tea.

Plant:

*Height.*—Approximately 90 to 100 cm on average at the end of the growing season.

*Width.— approximately* 60 cm on average at the end of the growing season.

Branches:

*Color.— Young stems: near Yellow-Green Group* 146C with some Greyed-Orange Group 175C and 175D. Adult wood: near Yellow-Green Group 148A.

*Thorns.*—On young stems: small prickles: quantity: none. Long prickles: configuration: upright. Quantity: approximately 6 on average on a stem length of 10 cm. Length: approximately 0.8 cm on average. Color: greyed-orange in coloration. on adult stems: small prickles: quantity: approximately 4 on average on a stem length of 10 cm. Length: approximately 0.7 cm on average. Color: near Greyed-Orange Group 164A. Long prickles: configuration: curved downwards on the upper surface, and concave on the under surface with an oval base. Quantity: approximately 18 on average on a stem length of 10 cm. Length: approximately 0.8 cm on average. Color: near Grey-Brown Group 199B.

Leaves:

*Stipules.*—Smooth, adnate, pectinate, and rather broad.

*Petioles.*—Upper surface: near Yellow-Green Group 147B in coloration. Under surface: near Yellow-Green Group 147C in coloration. Length: approximately 2 cm for the terminal leaflet on average. Texture: non-glandular on the upper surface, and with a very few prickles on the under surface.

*Rachis.*—Upper surface: near Yellow-Green Group 148C in coloration. Under surface: near Yellow-Green Group 148A in coloration. Texture: smooth.

*Leaflets.*—Number 3, 5 (most often), and 7. Shape: generally elliptical with a cuspidate tip and a rounded and obtuse base. Size: the terminal leaflets commonly are approximately 5 to 7 cm in length on average and approximately 3.5 to 4.8 cm in width on average. Serration: small and single (as illustrated). Texture: physically firm and thick. Color (young foliage): upper surface: near Yellow-Green Group 147A suffused with near Greyed-Orange Group 175C and 175D. Under surface: near Greyed-Orange Group 177A. Color (adult foliage): upper surface: near Yellow-Green Group 147A. Under surface: near Yellow-Green Group 147B.

Inflorescence:

*Number of flowers.*—Commonly approximately 1 to 3 blossoms per stem.

*Peduncle.*—Smooth, approximately 5 cm in length on average, approximately 0.3 cm in diameter on average, and near Green Group 143C with some Greyed-Orange Group 175C and 175D in coloration.

*Sepals.*—Upper surface: tomentose and near Yellow-Green Group 147D in coloration. Under surface: smooth and near Yellow-Green Group 146C with some Greyed-Orange Group 175C and 175D in coloration. Size: approximately 3.5 cm in length on average, and approximately 1.1 cm in width at the widest point on average.

*Buds.*—Shape: substantially conical. Size: large. Length: approximately 4.5 cm on average. Width: approximately 4.5 cm at the widest point on average. Color as calyx breaks: upper surface: near Red Group 36C, and suffused with near Red Group 56C. Under surface: near Red Group 36C.

*Flower.*—Shape: cup-shaped. Diameter: approximately 13 to 14 cm on average. Color (in the course of opening): upper surface: near Red Group 36C suffused with near Red Group 56C. Under surface: near Red Group 36C. Spot at base: near Yellow-Green Group 150C and commonly bearing a tiny spot of Red Group 36C. Upper side: near Red Group 36C. Color (open flower): upper side: near Red Group 36D. Under side: near Red Group 36D. Spot at base: on the under surface near Yellow-Green Group 150C and commonly bearing a tiny spot of Red Group 36C. Color stability: very slight change with age. Fragrance: highly fragrant and similar to that of Rosy Verbena. Lasting quality: the blossoms commonly last approximately 9 days on the plant on average. Since the plant is primarily intended for growing outside, the vase life of the blossoms has not been evaluated to date. Petal number: approximately 37 on average under normal growing conditions. Petal shape: with a substantially rounded tip and an obtuse base. Petal texture: consistent and somewhat firm. Petal length: approximately 5.4 cm on average. Petal width: approximately 4.7 cm on average. Petal arrangement: imbricated, and without petaloids. Petal drop: good with the petals commonly detaching cleanly before drying. Stamen number: approximately 166 on average. Anthers: regularly arranged in a whorl around the styles, approximately 0.3 cm in size on average, and near Yellow-Orange Group 21A in coloration. Pollen: present, and near Yellow Group 4D in coloration. Filaments: variable in length and approximately 0.2 to 0.8 cm in length on average, and near Yellow-Orange Group 21C in coloration. Pistils: approximately 159 on average. Stigmas: approximately 0.1 cm in size on average, and near Yellow Group 4D in coloration. Styles: approximately 0.2 cm in length on average, and near Red Group 53A in coloration. Receptacle: smooth, funnel-shaped in longitudinal section, approximately 0.9 cm in length on average, approximately 1.2 cm in width on average at the widest point, and near Green Group 143C in coloration. Hips: present.

Development:

*Vegetation.*—Very strong.

*Blooming.*—Mid-season, abundant and substantially continuous.

*Tolerance to diseases.*—Excellent, particularly with respect to Marsonia.

*Aptitude to bear fruit.*—Sparse to medium under observations to date.

I claim:

1. A new and distinct Hybrid Tea rose plant characterized by the following characteristics:

(a) forms very strong vegetation, (b) forms large substantially conical-shaped buds, (c) forms at mid-season abundantly and substantially continuously attractive highly fragrant Orient Pink blossoms, (d) displays attractive glossy dark green foliage, (e) displays excellent resistance to Marsonia, (f) is particularly well suited for providing attractive ornamentation in the landscape;

substantially as shown and described.

* * * * *

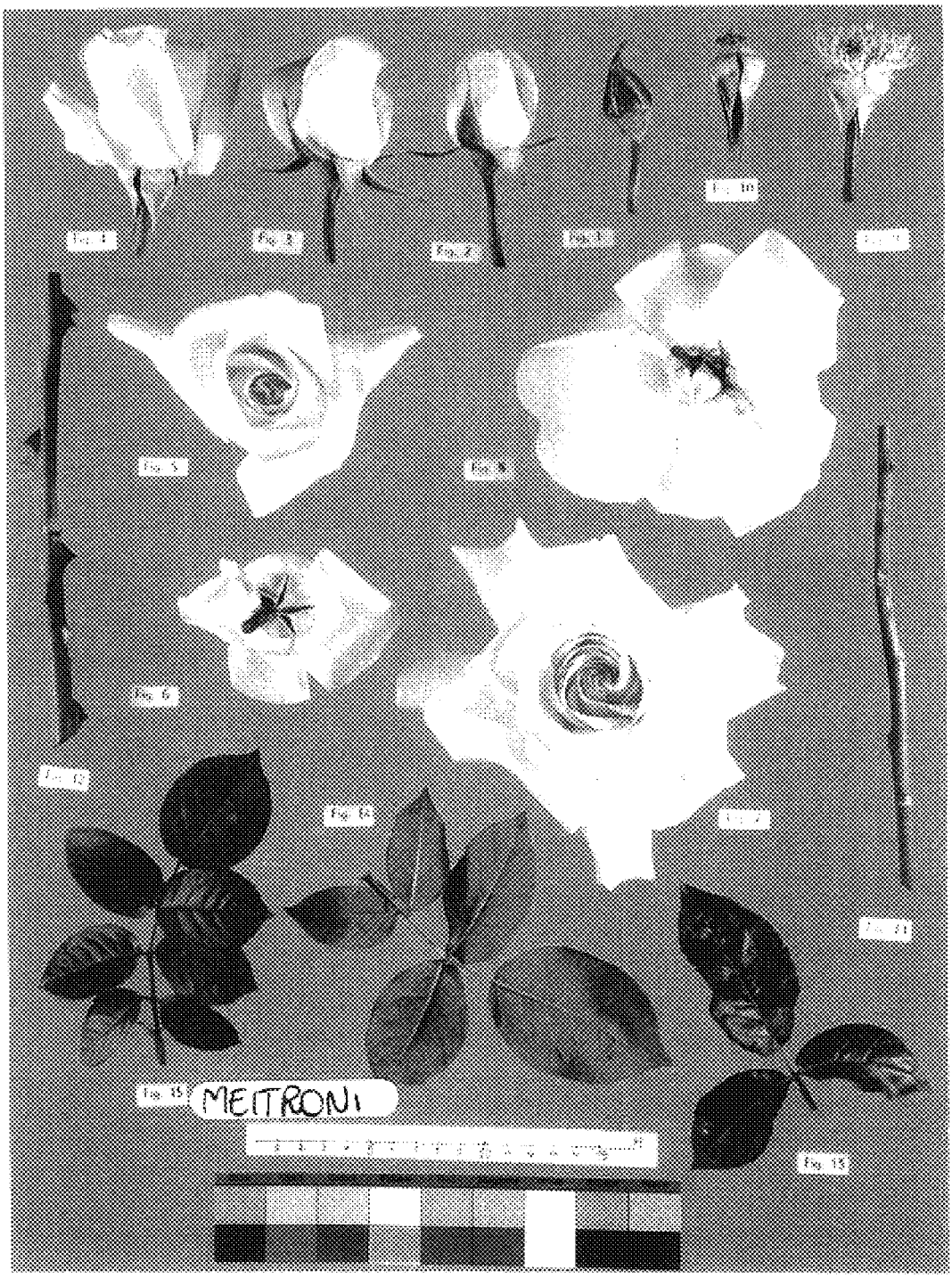
MEITRONI